(12) United States Patent
Guzman et al.

(10) Patent No.: US 8,801,312 B2
(45) Date of Patent: Aug. 12, 2014

(54) ANTISEPTIC APPLICATOR

(75) Inventors: Manuel Guzman, El Paso, TX (US);
Kyle W. Boone, El Paso, TX (US);
Miguel Rivera, El Paso, TX (US)

(73) Assignee: Carefusion 2200, Inc., San Diego, CA (US)

( * ) Notice: Subject to any disclaimer, the term of this patent is extended or adjusted under 35 U.S.C. 154(b) by 188 days.

(21) Appl. No.: 13/328,460

(22) Filed: Dec. 16, 2011

(65) Prior Publication Data

US 2013/0156486 A1 Jun. 20, 2013

(51) Int. Cl.
*B43K 5/14* (2006.01)

(52) U.S. Cl.
USPC ............... 401/134; 401/133; 401/132; 604/3

(58) Field of Classification Search
USPC ....................................... 401/132–135; 604/3
See application file for complete search history.

(56) References Cited

U.S. PATENT DOCUMENTS

| | | | |
|---|---|---|---|
| 4,415,288 A * | 11/1983 | Gordon et al. ............. | 401/132 |
| 5,769,552 A * | 6/1998 | Kelley et al. ............... | 401/132 |
| 6,505,985 B1 * | 1/2003 | Hidle et al. ................. | 401/134 |
| 6,910,822 B2 * | 6/2005 | Hidle et al. ................. | 401/134 |
| 6,916,133 B2 * | 7/2005 | Hoang et al. ............... | 401/133 |
| 7,241,065 B2 * | 7/2007 | Tufts et al. .................. | 401/133 |
| 7,306,390 B2 * | 12/2007 | Quintero et al. ........... | 401/133 |
| 7,648,296 B2 * | 1/2010 | Wong .......................... | 401/134 |
| 7,866,907 B2 * | 1/2011 | Cable et al. ................ | 401/134 |
| 8,113,731 B2 * | 2/2012 | Cable et al. ................ | 401/134 |
| 8,348,913 B2 * | 1/2013 | Hoang et al. ............... | 604/310 |
| 2012/0219347 A1 * | 8/2012 | Law et al. ................... | 401/133 |

* cited by examiner

*Primary Examiner* — David Walczak
*Assistant Examiner* — Jennifer C Chiang
(74) *Attorney, Agent, or Firm* — Arent Fox LLP

(57) ABSTRACT

An applicator assembly includes a head portion having a proximal, a distal end, and an interior portion defining a fluid chamber, a container slidably coupled to the body, a breakable membrane sealing an end of the container, and a hollow puncture mechanism, wherein the hollow puncture mechanism is mounted in the interior portion of the head portion and an interior of the container is placed in fluid communication with the application member by way of a fluid conduit that is formed through the hollow puncture mechanism from the container to the fluid chamber when the container is axially translated toward the head portion and the puncture mechanism pierces the breakable membrane.

28 Claims, 2 Drawing Sheets

ANTISEPTIC APPLICATOR

BACKGROUND

1. Field

The present disclosure relates to an antiseptic applicator and method of use thereof, and more particularly, to a puncture membrane antiseptic applicator that requires the application of opposing forces to actuate release of a sealed solution, preferably an antimicrobial solution, from a self-contained reservoir toward a material arranged at a distal end of the applicator for receiving the solution.

2. Description of Related Art

Antiseptic applicators for the preparation of a patient prior to surgery, for example, are known and common in the prior art. Conventional applicators rely on various means of actuation to release a self-contained reservoir of antimicrobial solution for sterilization of the patient's skin. For example, a number of applicators are designed with a puncturing means. These applicators typically include a head with a spike, for example, and a sealed container or cartridge. A push or screw motion is employed to axially translate the head toward the sealed container so that the spike may pierce the sealed container and effectuate the release of the solution contained therein. Some examples of applicators using a puncturing means include U.S. Pat. Nos. 4,415,288; 4,498,796; 5,769,552; 6,488,665; and 7,201,525; and U.S. Pat. Pub. No. 2006/0039742.

Other conventional applicators rely on breaking an internally situated frangible container or ampoule through the application of a one-way directional force or a localized application of pressure. The directional force is typically applied longitudinally to one end of the ampoule by a pushing motion designed to force the ampoule to break under a compressive stress, sometimes at a predetermined area of stress concentration. Alternatively, a pressure may be applied to a localized section of the ampoule through a squeezing motion designed to crush a section of the frangible ampoule in order to release the antimicrobial solution contained therein. Some examples of applicators using frangible ampoules in the manner discussed above include U.S. Pat. Nos. 3,757,782; 5,288,159; 5,308,180; 5,435,660; 5,445,462; 5,658,084; 5,772,346; 5,791,801; 5,927,884; 6,371,675; and 6,916,133.

Conventional antiseptic applicators, as described above, often require special packaging and/or handling during shipping and prior to use. For example, with the puncture type applicators, preventive measures are required to prevent an inadvertent push against either end of the device that may result in the puncturing of the sealed container and the premature discharge of the solution. A user must often use both hands to effectively overcome the preventive measures and activate the applicator for use. In addition, conventional antiseptic applicators often rely on the exertion of pressure on the walls of an applicator, for example, to break a frangible ampoule or squeeze the solution from the container toward an application material. The use of frangible ampoules requires special care to avoid breaking as a result of inadvertent pressure or dropping during shipping or prior to use. Furthermore, the components of a conventional applicator, such as the broken ampoule or the puncture spike, often impede the free flow of the solution from the container. There exists a need in the field for a novel antiseptic applicator that avoids the complications associated with conventional applicators, especially an applicator that will allow for effective one hand actuation and application of a solution without impediments to the free flow of the solution from the container to the application material.

SUMMARY

In accordance with aspects of the present invention, an applicator assembly may include a head portion having a proximal, a distal end, and an interior portion defining a fluid chamber, a container slidably coupled to the body, a breakable membrane sealing an end of the container, and a hollow puncture mechanism, wherein the hollow puncture mechanism is mounted in the interior portion of the head portion and an interior of the container is placed in fluid communication with the application member by way of a fluid conduit that is formed through the hollow puncture mechanism from the container to the fluid chamber when the container is axially translated toward the head portion and the puncture mechanism pierces the breakable membrane.

In accordance with another aspect of the present invention, the applicator assembly may further include a separable closing member sealing the other end of the container from the end having the breakable membrane.

In accordance with another aspect of the present invention, the applicator assembly may include an annular retention ring provided on an exterior of a sidewall of the container for mating with a first annular retention channel configured into an interior of the head portion to apply resistance to the axial movement of the container in relation to the head portion.

In accordance with yet another aspect of the present invention, the applicator assembly may include a second annular retention channel configured into the interior of the head portion and disposed closer toward the distal end than the first annular retention channel.

In accordance with another aspect of the present invention, a mechanical stop may be provided to secure the container in a predetermined position until the stop is released prior to actuation of the applicator.

In accordance with other aspects of the present invention, the hollow puncture mechanism may include a transverse fluid conduit to provide fluid communication from an exterior portion of the puncture mechanism into the hollow puncture mechanism.

It will become readily apparent to those skilled in the art from the following detailed description, wherein it is shown and described only exemplary configurations of an applicator assembly. As will be realized, the invention includes other and different aspects of an applicator and assembly and the various details presented throughout this disclosure are capable of modification in various other respects, all without departing from the spirit and scope of the invention. Accordingly, the drawings and the detailed description are to be regarded as illustrative in nature and not as restrictive.

DETAILED DESCRIPTION

Figure 1:
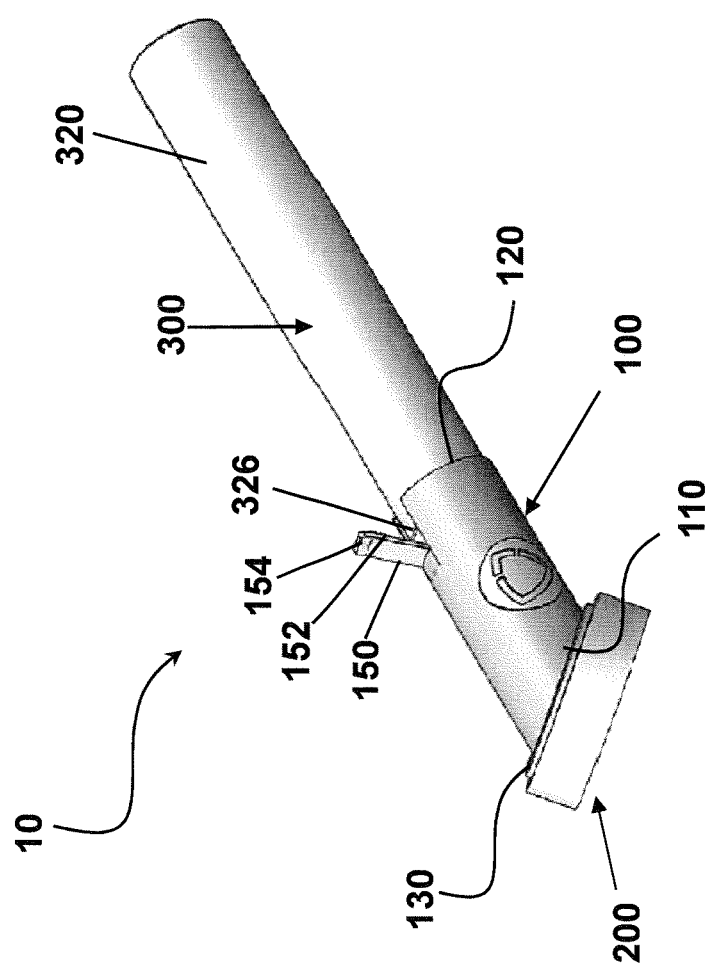
FIG. 1 is a perspective view of an antiseptic applicator, in accordance with certain aspects of the present invention.

Various aspects of an antiseptic applicator may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of an antiseptic applicator in addition to the orientation depicted in the drawings. By way of example, if an antiseptic applicator in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of an antiseptic applicator disclosed herein.

Figure 2:
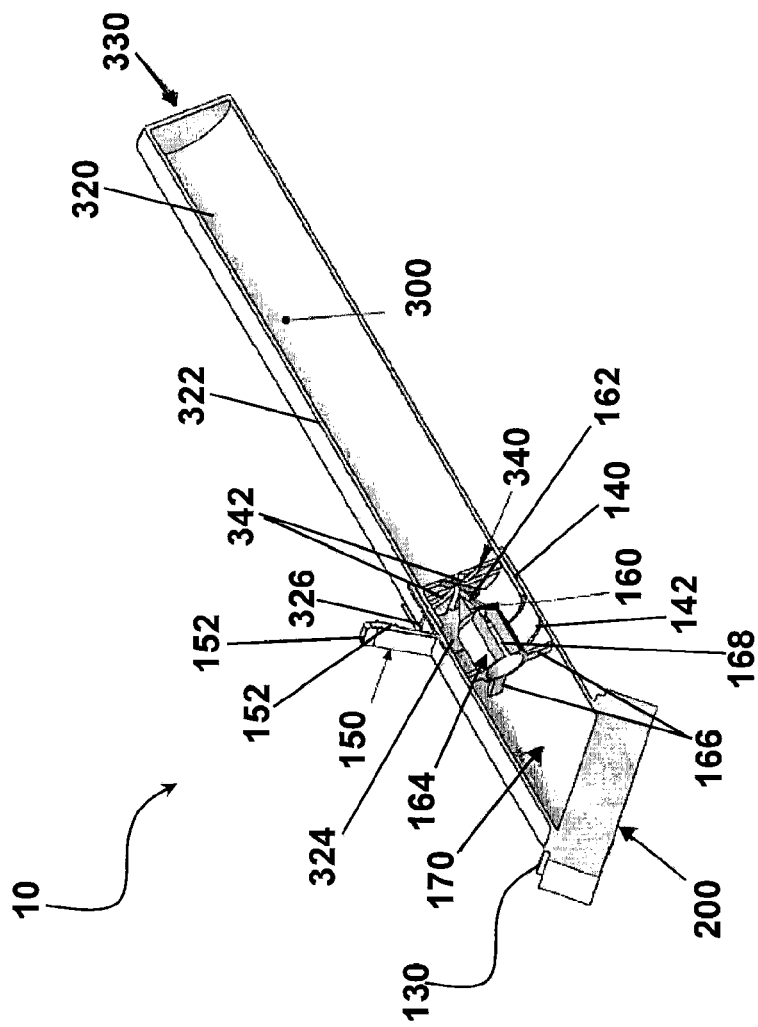
FIG. 2 is a side cutaway view of an antiseptic applicator, in accordance with certain aspects of the present invention.

The antiseptic applicator may be compact and ergonomically designed. As shown in FIGS. 1 and 2, an antiseptic applicator 10 may comprise a substantially hollow head portion 100, which may be cylindrical in shape, an application member 200 mounted to or proximate to a distal end 110 of the head portion 100, and a solution container 300 slidably received by a proximal end 120 of the head portion 100. The solution container 300 may be cylindrical in shape to position concentrically into the head portion 100 with a proximal end 320 extending beyond the proximal end 120 of the head portion 100. The solution container may be formed with a grasping mechanism, such as an area of cross-hatching, for example, or a raised or recessed area integrated into a side wall 322 of the container 300, to enhance the ability of a user to hold and/or push the solution container 300 in one direction with one hand, in order to translate the solution container 300 in an axial direction toward the distal end 110 of the head portion 100.

The application member 200 may be formed from a foam sponge material, for example, or any suitable material that allows the controlled application of the contained solution from the solution container 300 to a surface external to the applicator 10. The material chosen may be porous with a particular soak rate, for example, or may be provided with structural features, including slits or apertures, to direct and control the flow rate of the solution through the application member 200. The head portion 100 may be configured to have a mounting flange 130 at or proximate to the distal end 110. The mounting flange 130 provides a surface for affixing the application member 200 to the head portion 100.

The solution container 300 is preferably a self-contained structure, formed of a suitable material, such as a polymer, preferably a high-density polyethylene plastic, that is flexible, yet resistant to deformation and chemical leaching. The container 300 may be filled with various liquids such as antiseptics or medicaments, chemical compositions, cleansing agents, cosmetics, or the like, and preferably an antimicrobial liquid or gel composition, such as a solution containing an alcohol, aldehyde, anilide, biguanide (i.e., chlorhexidine gluconate), diamidine, halogen-releasing agent, silver compound, peroxygen, and or phenols, for antiseptic application to a patient prior to surgery. The container 300 is designed to withstand various heat and chemical sterilization techniques, which may be performed sequentially with a solution filling process, in accordance with techniques that are well known in the art, such as a blow-fill-seal technique.

As shown in FIG. 2, the container 300 may be an elongated cylinder formed by the sidewall 322. A closing member 330 may be provided at the proximal end 320 and a breakaway membrane 340 formed toward an insertion end 324 of the container 300 to seal shut an interior of the container 300. The closing member 330 may be integrally formed with the container 300 or, for example, may be a separate component connected to the container, such as an end cap 330 for mating via a threaded connection with the proximal end 320, or a plug that may be press fit or heat welded to the container 300, for sealing shut the open proximal end 320. Thus, in accordance with certain aspects of the present invention, with the breakaway membrane 340 in place, solution may be filled through the open proximal end 320 of the container 330 prior to the container 300 being sealed shut with the closing member 330.

The breakaway membrane 340 may be formed of a suitable material, such as a foil or a high-density polyethylene plastic, having enough strength to effectively seal the insertion end 324 of the container 300 and prevent leaching of the contained solution. The breakaway membrane 340 may be formed with break channels 342, which may be channels of thinner material designed to permit the breakaway membrane 340 to break or tear in a predetermined pattern when punctured.

As shown in FIGS. 1 and 2, the sealed container 300 having a solution contained therein may be slidably inserted into the proximal end 120 of the head portion 100. A retaining member, such as an annular retention ring 326, may be provided on the exterior of the side wall 322 toward the insertion end 324 of the container 300. The retaining member may cooperate with a corresponding member on the head portion 100, such as a first annular retention channel 140 configured into an interior of the head portion 100 to limit the axial movement of the container 300 in relation to the head portion 100 and to prevent the separation of the container 300 from the head portion 100 once joined in a final assembled position. In accordance with yet other aspects of the present invention, the retaining member may be provided on the head portion 100 and cooperate with a corresponding member on the container 300 to prevent the separation of the container 300 from the head portion 100.

In accordance with yet another aspect of the present invention, a mechanical stop 150 may be provided to secure the container 300 in the assembled position until the stop 150 is intentionally released prior to actuation of the applicator 10. In this manner, a puncture mechanism 160 attached to or integral to an interior fluid chamber 170 of the head portion 100 may be prevented from rupturing the breakaway membrane 340 during handling, storage and transport of the applicator 10. The mechanical stop 150 may be attached to or integral to the proximal end 120 of the head portion 100. In accordance with another aspect of the present invention, the mechanical stop may alternatively be provided on a portion of the container 300. A securing mechanism 152, such as a snap fit channel, for example, may be provided on an inner side of the securing mechanism to engage the retaining member when the mechanical stop 150 is pressed against the container 300, or against the head portion 100 in an alternative configuration, to be maintained a storage position. With the securing mechanism 152 thus engaged, the container 300 may be prevented from axial movement toward and away from the head portion 100 during assembly, handling or transport of the applicator 10. To disengage the mechanical stop 150, a user simply applies pressure against a release tab 154 to maneuver the mechanical stop 150 away from the container 300, or head portion 100 in an alternative configuration, and disengage the securing mechanism 152. The release tab 154 may be angled to provide clearance between the stop 150 and the container 300 when the stop 150 is hinged in a closed position with the securing mechanism 152 engaged. A user may thus easily disengage the stop 150 with one hand by applying pressure with one finger, such as a thumb or index finger, against the release tab 154 while holding the applicator 10.

In accordance with other aspects of the present invention, the mechanical stop 150 may be formed with a detent on an interior surface (not shown) to further prevent axial movement of the container 300 toward the head portion 100. The detent may extend into the interior portion of the head portion 100 near where the stop 150 is hinged and engage the insertion end 324 of the container 300 when in a closed position. Alternatively, if the mechanical stop is provided on a portion of the container 300, the detent may extend into the interior portion of the container 300, and engage the corresponding end of the head portion 100. Upon the rotational release of the stop 150 by pressure exerted against the release tab 154, the detent rotates along with the stop 150 and releases the insertion end 324 of the container to slide into the head portion 100. The stop 150 may be configured to lock into an open position once actuated.

As shown in FIG. 2, with the container 300 concentrically mounted in the head portion 100, as described above, and the application member 200 mounted to close off the distal end 110 of the head portion 100, the fluid chamber 170 may be formed in the distal end of the head portion 100 between the application member 200 and the breakaway membrane 340. A fluid metering device, such as a pledget, for example, may be optionally provided in the fluid chamber 170 to further control and/or direct the flow of solution from the container 300 when the assembly 10 is in use.

To activate the applicator 10 and release the solution from the container 300, a user may grasp the container 300 with one hand. The mechanical stop 150 may be disengaged by using a finger on the same hand to exert pressure against the release tab 154 and disengage the securing mechanism 152. The user may either use their other hand to hold the head portion 100 and/or may press the head portion 100 against a stable surface while applying force against the container 300 to slide the container into the head portion 100. The application of the compressive force dislodges the retention ring 326 from the first annular retention channel 140, allowing the container 300 to translate from a proximally disposed position further into the head portion 100. Continued applied force on the container 300 axially translates the container 300 toward the distal end of the head portion 100.

As shown in FIG. 2, the puncture mechanism 160 may be formed with a hollow tip portion 162 and a hollow body portion 164. Support struts 166 may be provided to secure the body portion 164 of the puncture mechanism 160 at a predetermined position in the head portion 100 of the applicator 10. As the container 300 translates toward the distal end 110 of the head portion 100, the tip portion 162 punctures or tears the breakaway membrane 340. With the membrane 340 thus compromised, via the positioning of the applicator 10 with the application member 200 situated below the container 300, the solution drains from the container 300 into the fluid chamber 170 under its own weight. Further axial translation of the container 300 in a distal direction relative to the head portion 100 may accelerate the rupturing of the breakaway membrane 340, which may increase the flow of the solution from the container 300 into the fluid chamber 170.

As shown in FIG. 2, the puncture mechanism 160, by virtue of being hollow, may form a fluid channel through the interior portion of the puncture mechanism 160. A transverse fluid conduit 168, such as the longitudinal gap shown in FIG. 2, for example, or orifices provided in the tip portion 162 and/or the body portion 164 of the puncture mechanism 160, allows fluid to be communicated from an exterior portion of the puncture mechanism 160, through the hollow puncture mechanism 160, and directly into the fluid chamber 170, whether or not fluid is being blocked from passage around the puncture mechanism 160. Thus, if for any reason the fluid passage around the puncture mechanism 160 is blocked, continued insertion of the container 300 into the head portion 100 will allow for at least portions of the fluid conduit 168 to breach the membrane 340 and provide communication from the interior of the container 300 and the fluid chamber 170. The solution may soak into, or otherwise flow through, the application material 200 at a specified volume and rate. The fluid chamber 170 may serve to accumulate and distribute the solution evenly over substantially the entire area of the application material 200. Once the application material 200 is engorged, for example, the solution may then be applied to a patient by wiping the distal surface of the application material 200 against the skin.

According to another aspect of the present invention, a second retaining member, such as a second annular retention ring 142 may be provided along the interior of the head portion 100 that is disposed closer toward the distal end 110 than the first retaining member. The retention ring 326 on the container 300 may thus engage the second annular retention ring 142 after a predetermined distance of translation into the head portion 100 to substantially secure the container 300 and maintain the applicator 10 in an open position.

The previous description is provided to enable any person skilled in the art to practice the various embodiments described herein. Various modifications to these embodiments will be readily apparent to those skilled in the art, and the generic principles defined herein may be applied to other embodiments. For example, rather than the container 300 being concentrically mounted in the head portion 100, the head portion 100 may slidably mount into the container 300. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An applicator assembly comprising:
    a head portion having a proximal end, a distal end, and an interior portion defining a fluid chamber;
    a container slidably coupled to the head portion;
    a breakable membrane sealing an end of the container;
    an application member attached to the distal end; and a hollow puncture mechanism comprising:
   a hollow tip portion;
   a hollow body portion; and
   a transverse fluid conduit to provide fluid communication from an exterior portion of the puncture mechanism into the hollow puncture mechanism,
wherein the puncture mechanism is mounted in the interior portion of the head portion and an interior of the container is placed in fluid communication with the application member by way of a fluid conduit that is formed through the hollow puncture mechanism from the container to the fluid chamber when the container is axially translated toward the head portion and the puncture mechanism pierces the breakable membrane.

2. The applicator assembly of claim 1, further comprising a closing member sealing the other end of the container from the end having the breakable membrane.

3. The applicator assembly of claim 2, wherein the closing member is separable from the container.

4. The applicator assembly of claim 3, wherein the closing member is connected to the container via a threaded connection.

5. The applicator assembly of claim 1, further comprising an annular retention ring provided on an exterior of a sidewall of the container for mating with a first annular retention channel configured into an interior of the head portion to apply resistance to the axial movement of the container in relation to the head portion.

6. The applicator assembly of claim 5, further comprising a second annular retention channel configured into the interior of the head portion and disposed closer toward the distal end than the first annular retention channel.

7. The applicator assembly of claim 1, further comprising a mechanical stop to secure the container in a predetermined position until the stop is released prior to actuation of the applicator.

8. The applicator assembly of claim 7, wherein the mechanical stop comprises a hinged portion of the proximal portion of the head portion.

9. The applicator assembly of claim 8, wherein the mechanical stop further comprises a securing mechanism to prevent axial translation of the container.

10. The applicator assembly of claim 9, wherein the securing mechanism comprises a snap fit channel for engaging a retention ring on an exterior of the container to secure the applicator assembly in a storage position when the mechanical stop is pressed against the container.

11. The applicator assembly of claim 8, wherein the securing mechanism comprises a detent that engages an insertion end of the container.

12. The applicator assembly of claim 1, wherein the hollow puncture mechanism further comprises support struts that extend radially from the hollow body portion to secure the hollow puncture mechanism at a predetermined position in the head portion.

13. The applicator assembly of claim 1, wherein the tip portion pierces the breakaway membrane when the container translates toward the distal end of the head portion.

14. The applicator assembly of claim 1, wherein the transverse fluid conduit comprises a gap extending longitudinally along the hollow tip portion and the hollow body portion.

15. An applicator assembly comprising:
   a head portion having a proximal end, a distal end, and an interior portion defining a fluid chamber;
   a container slidably coupled to the head portion;
   a breakable membrane sealing an end of the container;
   an application member attached to the distal end; and
   a hollow puncture mechanism comprising:
      a hollow tip portion;
      a hollow body portion having an outlet portion; and
      support struts that extend radially from the outlet portion of the hollow body portion to secure the hollow puncture mechanism at a predetermined position in the head portion,
   wherein the puncture mechanism is mounted in the interior portion of the head portion and an interior of the container is placed in fluid communication with the application member by way of a fluid conduit that is formed through the hollow puncture mechanism from the container to the fluid chamber when the container is axially translated toward the head portion and the puncture mechanism pierces the breakable membrane.

16. The applicator assembly of claim 15, further comprising a closing member sealing the other end of the container from the end having the breakable membrane.

17. The applicator assembly of claim 16, wherein the closing member is separable from the container.

18. The applicator assembly of claim 17, wherein the closing member is connected to the container via a threaded connection.

19. The applicator assembly of claim 15, further comprising an annular retention ring provided on an exterior of a sidewall of the container for mating with a first annular retention channel configured into an interior of the head portion to apply resistance to the axial movement of the container in relation to the head portion.

20. The applicator assembly of claim 19, further comprising a second annular retention channel configured into the interior of the head portion and disposed closer toward the distal end than the first annular retention channel.

21. The applicator assembly of claim 15, further comprising a mechanical stop to secure the container in a predetermined position until the stop is released prior to actuation of the applicator.

22. The applicator assembly of claim 21, wherein the mechanical stop comprises a hinged portion of the proximal portion of the head portion.

23. The applicator assembly of claim 22, wherein the mechanical stop further comprises a securing mechanism to prevent axial translation of the container.

24. The applicator assembly of claim 23, wherein the securing mechanism comprises a snap fit channel for engaging a retention ring on an exterior of the container to secure the applicator assembly in a storage position when the mechanical stop is pressed against the container.

25. The applicator assembly of claim 22, wherein the securing mechanism comprises a detent that engages an insertion end of the container.

26. The applicator assembly of claim 15, wherein the tip portion pierces the breakaway membrane when the container translates toward the distal end of the head portion.

27. The applicator assembly of claim 15, wherein the hollow puncture mechanism comprises a transverse fluid conduit to provide fluid communication from an exterior portion of the puncture mechanism into the hollow puncture mechanism.

28. The applicator assembly of claim 27, wherein the transverse fluid conduit comprises a gap extending longitudinally along the hollow tip portion and the hollow body portion.

* * * * *